United States Patent [19]

Ebling et al.

[11] 4,137,160

[45] Jan. 30, 1979

[54] DEVICE FOR SEPARATING LOW DENSITY MATERIAL SUCH AS GAS BUBBLES FROM A LIQUID, AND THE USE THEREOF IN A DIALYSIS DELIVERY SYSTEM

[75] Inventors: Wendell V. Ebling, Libertyville, Ill.; Rene G. Lamadrid, Bethesda, Md.; Earl G. Phillips, Wheeling, Ill.

[73] Assignee: Baxter Travenol Laboratories, Inc., Deerfield, Ill.

[21] Appl. No.: 739,878

[22] Filed: Nov. 8, 1976

Related U.S. Application Data

[63] Continuation of Ser. No. 519,730, Oct. 31, 1974, abandoned.

[51] Int. Cl.$^2$ ............................................. B01D 13/00
[52] U.S. Cl. ..................... 210/22 A; 210/87; 210/188; 210/195 R; 210/321 B
[58] Field of Search ............... 55/204, 191; 210/512, 210/87, 321 B, 22, 96, 188, 15, 196, 197

[56] References Cited

U.S. PATENT DOCUMENTS

| 2,231,501 | 2/1941 | Jepertinger | 55/191 X |
| 2,545,028 | 3/1951 | Haldeman | 55/204 X |
| 3,235,090 | 2/1966 | Bose et al. | 210/512 R |

Primary Examiner—Frank A. Spear, Jr.
Attorney, Agent, or Firm—Garrettson Ellis; Paul C. Flattery

[57] ABSTRACT

A device, which may be used in a dialysis system, is disclosed for separating low density material such as gas bubbles from a liquid by swirling the liquid, to cause the bubbles to migrate toward the center of the swirling liquid. A liquid storage chamber having side walls of generally circular cross-section of the longitudinal axis is provided. A port is provided for removing the bubbles or the like, positioned adjacent the longitudinal axis of the chamber. A liqud inlet passes into the chamber in such a position as to pass liquid into the chamber circumferentially about the side walls, to provide swirling of liquid passing into the chamber. In accordance with this invention, outlet means and pump means are provided for removing bubble-free liquid from the chamber at a point spaced from the inlet but adjacent the side wall. A first conduit conveys a portion of the bubble-free liquid so removed to a desired site of use, while a second conduit conveys the balance of the bubble-free liquid so removed back to the liquid inlet for reentry into the chamber, to enhance the swirling action of fluid in the chamber.

10 Claims, 5 Drawing Figures

DEVICE FOR SEPARATING LOW DENSITY MATERIAL SUCH AS GAS BUBBLES FROM A LIQUID, AND THE USE THEREOF IN A DIALYSIS DELIVERY SYSTEM

This is a continuation of application Ser. No. 519,730, filed Oct. 31, 1974, now abandoned.

BACKGROUND OF THE INVENTION

This application relates to novel apparatus, which may be used in a dialysis delivery system for blood dialysis or the like and which provides a means for removing bubbles or other low density materials from a liquid, while at the same time providing pressurized, bubble-free liquid to its desired point of use.

In blood dialysis, blood is passed through a dialysis unit on one side of a membrane of cellulose or the like, and dialysis solution is passed across the other side of the membrane, containing a sufficient concentration of salt to render the dialysis solution generally isotonic with respect to the blood. During dialysis, unwanted materials such as urea, creatinine, and some water pass through the membrane from the blood into the dialysis solution, so that the dialyzer serves the function of the natural kidney in many important ways.

There are many different designs of apparatus for supplying the dialysis solution to the dialysis unit. One well-known design is the RSP Dialyzer sold by Travenol Laboratories, Inc. of Deerfield, Ill. This apparatus provides large quantities of dialysis solution to a coil-type artificial kidney, and recirculates a portion of the dialysis solution through the artificial kidney repeatedly, while constantly withdrawing a fraction of the spent dialysis solution and supplying a corresponding portion of fresh dialysis solution. This method of providing dialysis solution is commonly known as the recirculating single pass technique.

Other dialysis delivery systems which are available provide a lower quantity of dialysis solution to a Kiil-type, flat plate dialyzer or the like, in which the dialysis solution typically passes through a dialyzer in a single pass, and then is discarded.

In all instances of dialysis solution delivery to various dialyzers, it is desirable to remove air bubbles from the dialysis solution, since the air bubbles can block the capillary passages of the dialyzer and otherwise reduce its dialysis efficiency. The air bubbles are formed in particular when the dialysis solution is heated before use to a temperature which approximates body temperature, to avoid undue chilling of the patient during dialysis. As is well known, aqueous liquids which are warmed release some of the dissolved gases which are in them, to form bubbles.

It is desirable to have the capability of venting these gas bubbles to the atmosphere. However, at the same time, the dialysis solution is administered under pressure (either positive pressure, or reduced pressure caused by suction) to the artificial kidney. In both of these cases where the pressure is other than atmospheric, it becomes difficult to continuously vent the gas bubbles.

In accordance with this invention, a device is provided for separating low density materials such as gas bubbles from a liquid, and permitting the gas bubbles or the like to be vented or otherwise removed, while at the same time providing a pressurized, bubble-free liquid to the site of use, which is typically an artificial kidney.

DESCRIPTION OF THE INVENTION

The invention of this application constitutes an improvement upon the co-pending application, filed simultaneously herewith, of William J. Schnell and Ludwig Wolf, Jr., entitled "Swirling Flow Bubble Trap."

The device of this invention separates low density materials, and particularly gas bubbles, from a liquid by swirling the liquid to cause the bubbles to migrate toward the center of the swirling liquid. A liquid storage chamber is provided having side walls of generally circular cross-section about a longitudinal axis. A port is provided for removing the bubbles, the port being positioned adjacent to the longitudinal axis of the chamber and at its upper end in position of use. The device of this invention also has a liquid inlet to the chamber which is positioned to pass liquid into the chamber circumferentially about the side walls, to provide a swirling of liquid passing into the chamber.

In accordance with this invention, outlet means connected to pump means are provided for removing the bubble-free liquid from the chamber at a point spaced from the liquid inlet, but adjacent the side walls. First conduit means are provided for conveying a portion of the bubble-free liquid so removed to a desired site of use, for example, an artificial kidney. Second conduit means are provided for conveying the balance of the bubble-free liquid so removed to the liquid inlet again for reentry into the chamber through the liquid inlet, to enhance the swirling action of fluid in the chamber.

Accordingly, the pump mentioned above continuously provides a flow of bubble-free liquid, some of which may be diverted to the artificial kidney or other use, while the remainder of it is recirculated to the liquid inlet and forcefully expelled in circumferential manner about the inner circular side wall of the storage chamber, to create a continuous swirling vortex of fluid in the chamber. Bubbles and the like migrate to the center of the vortex, for collection in the removing port.

When required, liquid heating means, such as a conventional resistance heater, may be present in the chamber to heat the swirling liquid. The heater can function as a dialysis solution temperature control for the dialysis delivery system in which the device of this invention is installed. It is particularly advantageous for the heater to be present in the chamber, since bubbles are formed by the very act of heating, and they can accordingly be immediately removed by the device of this invention.

It is also desirable for flow restriction means to be present in the second conduit for conveying the balance of bubble-free liquid back to the chamber. This permits an elevated pressure zone to be present upstream from the flow restriction means and downstream from the pump means, which zone includes the first conduit. Accordingly, dialysis solution or the like can be supplied through the first conduit under any desired pressure, depending upon the power of the pump and the size of the flow restricter, to an artificial kidney or other device.

The venting means adjacent the longitudinal axis of the chamber for receiving air bubbles is preferably also adjacent the axis of liquid swirling within the chamber, and comprises an elongated, upstanding conduit for receiving pressurized liquid from the container. Accordingly, when the liquid within the chamber of circular cross-section is under pressure, for example from pressure imparted by the liquid head of a main dialysis solution supply tank, the upstanding conduit can receive a corresponding column of dialysis solution to create a counterbalancing pressure head, and prevent spillage from the container through the upstanding conduit, while still permitting the conduit to communicate with the atmosphere for venting.

An additional liquid replenishment conduit communicates with the chamber for connection to a liquid source, for replacement into the chamber of liquid delivered to a point of use through the first conduit. This liquid replenishment conduit may be connected to the second conduit for recirculation of dialysis solution or the like, and in the specific embodiment of this invention communicates with main dialysis solution storage tank.

Furthermore, it is preferable for the liquid inlet to be positioned adjacent the upper end of the chamber in position of use. Correspondingly, the outlet means is positioned at a lower end of the chamber and the heating means is spaced from the lower end. Accordingly, bubbles generated from the liquid by the heating means do not pass through the outlet means in normal operation, because they tend to rise, and move inwardly due to the flowing of the liquid, and thus do not reach the bottom of the liquid storage chamber.

Figure 1:
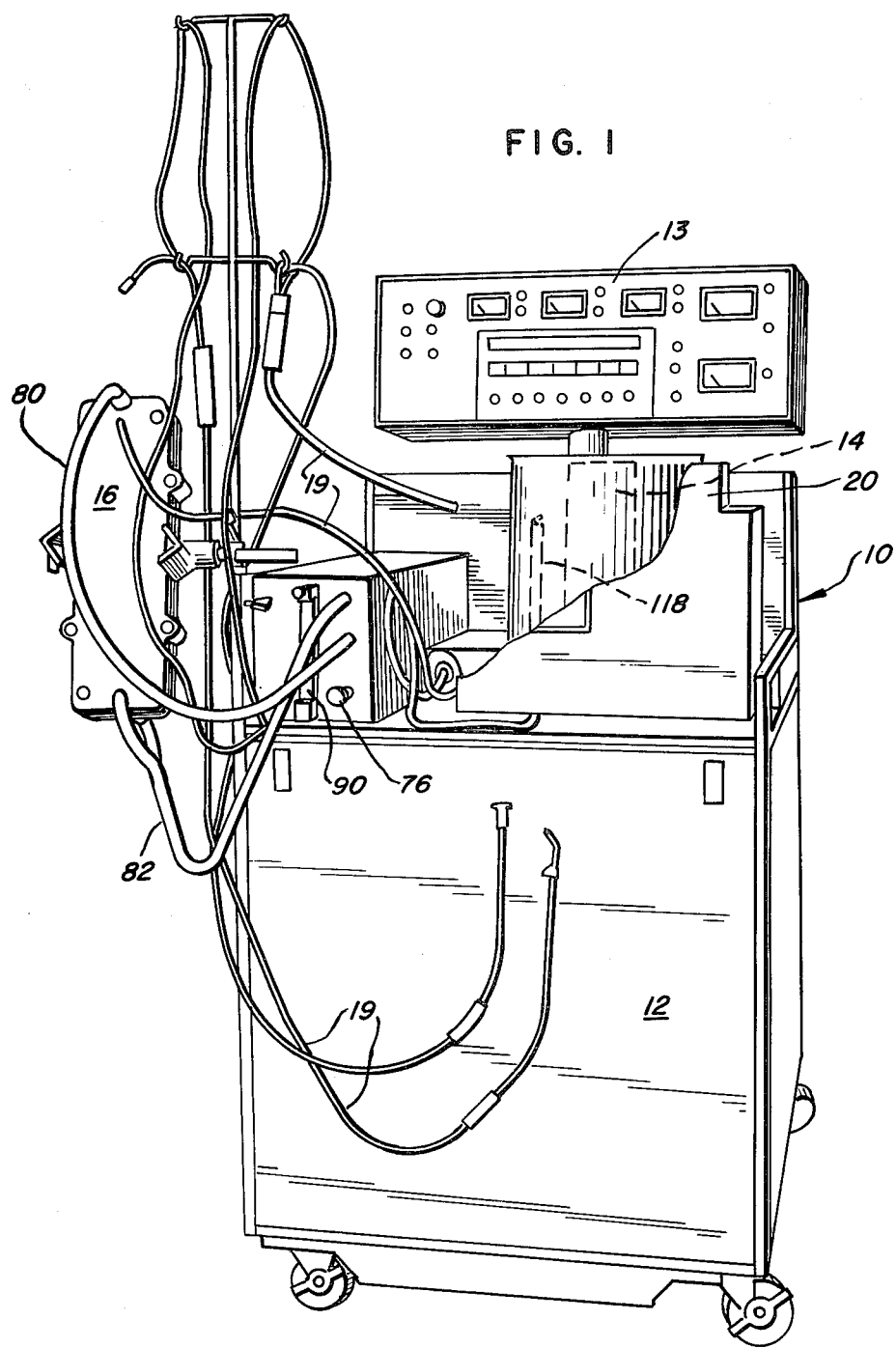
FIG. 1 is a perspective view of a dialysis delivery system incorporating the present invention, with a portion broken away.
Figure 2:
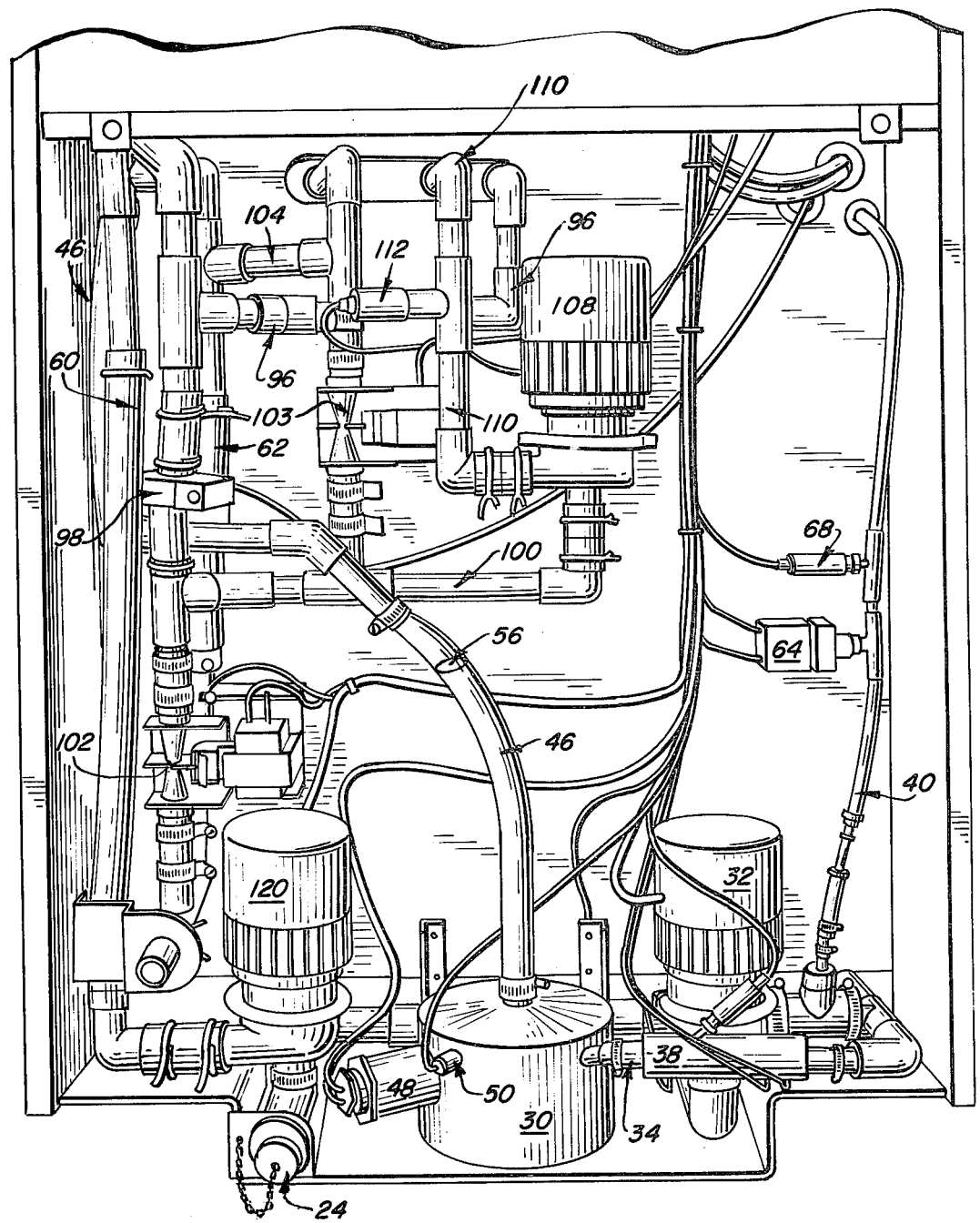
FIG. 2 is an elevational view of the rear of the dialysis solution delivery system of this invention.

Referring to the drawings, dialysis solution delivery system 10 is shown comprising a cabinet 12 containing the flow conduits and pumps used herein, and also carrying a pair of dialysis units 14, 16 for use in conjunction with the device of this invention. Dialysis unit 14 is shown to be a typical coil-type dialyzer which rests in container 18, and is adapted by the apparatus of this invention to receive dialysis solution in the recirculating-single pass mode of operation.

Dialysis unit 16 is shown to be a Kiil-type, flat plate dialyzer comprising a stack of alternating membrane pairs and flat sheet-like membrane supports. This dialysis unit is adapted by the apparatus of this invention for once-through, single pass flow of dialysis solution, after which the dialysis solution is disposed of. Alternatively, a hollow fiber type dialyzer or the like can be used in this mode.

It should be understood, that, conventionally, only one dialyzer at a time is used with the apparatus of this invention, although it is readily possible to adapt, by simple modification readily understandable to those skilled in the art, the device of this invention to service two or more dialysis units at the same time. The apparatus of FIG. 1 is shown in conjunction with two dialysis units in illustration of the fact that the system of this invention can be utilized to provide dialysis solution in either the single pass or the recirculating-single pass modes. Likewise, the apparatus of this invention can be adapted to recirculate the dialysis solution back to its storage tank if desired.

Blood pump 20 may be a conventional roller-type pump as is currently used in the presently known dialysis solution delivery systems. As is presently practiced, flexible plastic blood lines 19 pass through the roller pump, and communicate with the blood flow paths of the dialyzer, to be used to withdraw blood from the patient, to pass it through the dialyzer, and then to return it to the patient.

Figure 3:
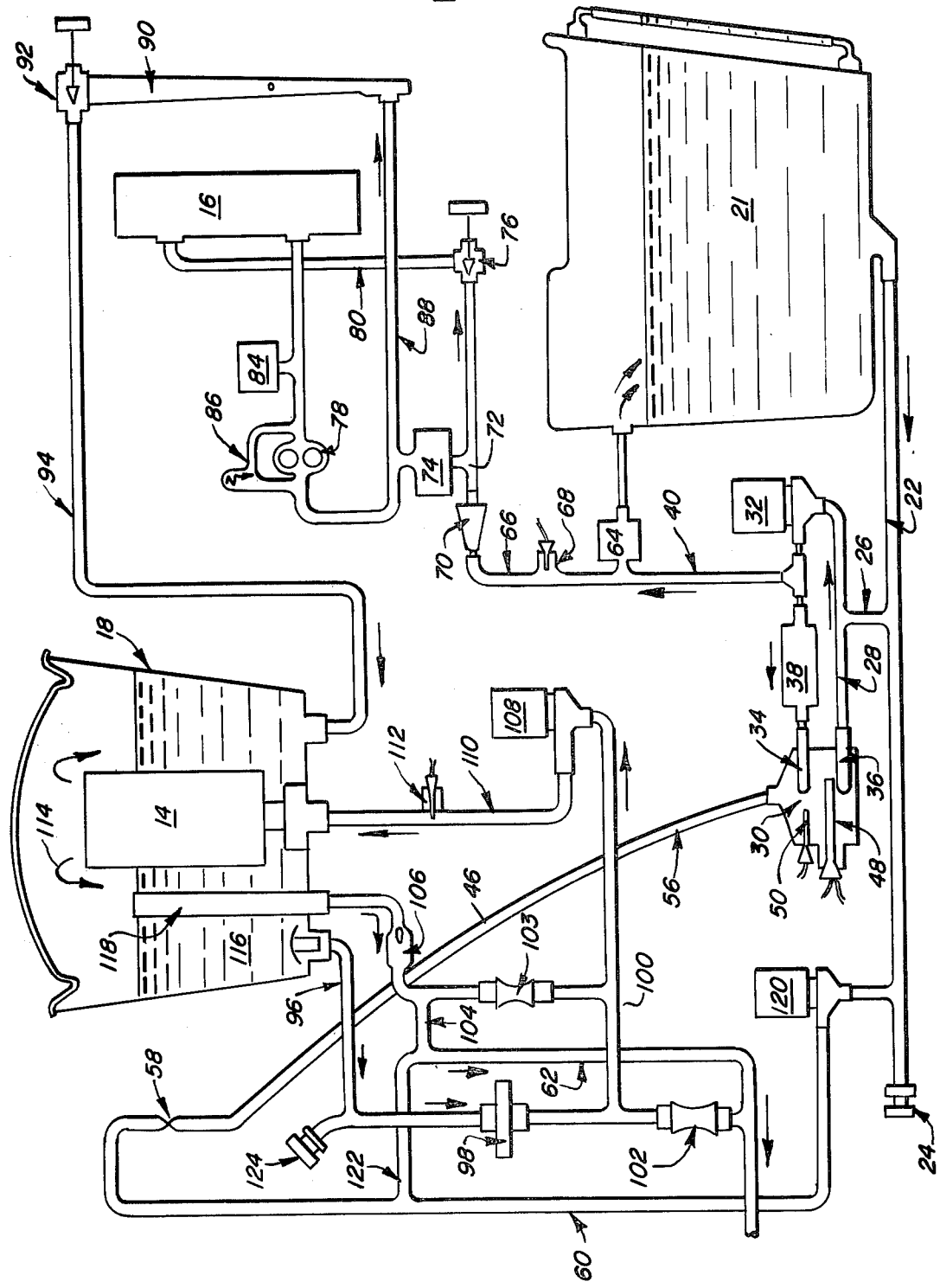
FIG. 3 is a schematic diagram of the various flow conduits and related parts of the dialysis solution delivery device of this invention.

Referring in particular to FIG. 3, but with reference to the remaining drawings, dialysis solution is stored in storage tank 21, which may conveniently have a capacity of about 200 liters in order to accomodate essentially all dialysis procedures.

Conduit 22 leads horizontally across the bottom of apparatus 10, and terminates in closable drain 24 which may be opened for final emptying from the system of liquid. Branching connection 26 provides communication between conduit 22 and line 28, which, in turn communicates between the liquid storage chamber 30 described above and the inlet of pump 32, which recirculates dialysis solution between outlet means 36 and liquid inlet 34 to chamber 30, both of which communicate with chamber 30. Upstream from inlet 34 is conductivity cell 38, which may be of conventional fabrication, or may be as disclosed in the application filed simultaneously herewith by Wendell V. Ebling and Herbert Goldsmith entitled "Improved Conductivity Monitoring System". Cell 38 monitors the electrolyte concentration of the dialysis solution to prevent injury to the patient by providing warning if the concentration of solution is wrong. The conductivity read by cell 38 is indicated on panel 13 of apparatus 10.

Fresh, bubble-free dialysis solution is conveyed under pressure from pump 32 through line 40 to either of the dialysis units 14, 16.

Figure 4:
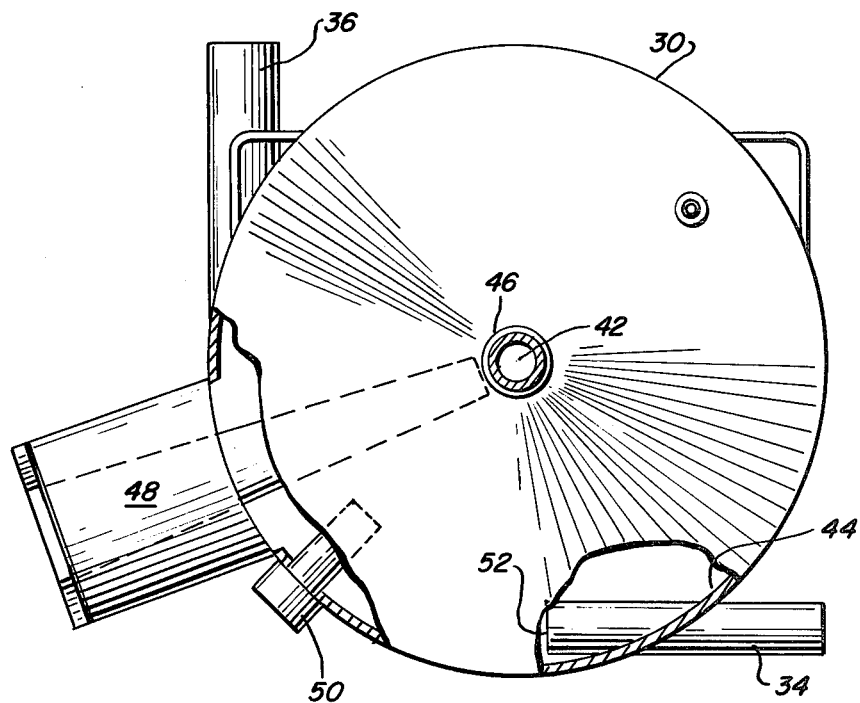
FIG. 4 is a plan view of the bubble separating device of this invention, in the specific embodiment used in the dialysis solution delivery system shown herein.
Figure 5:
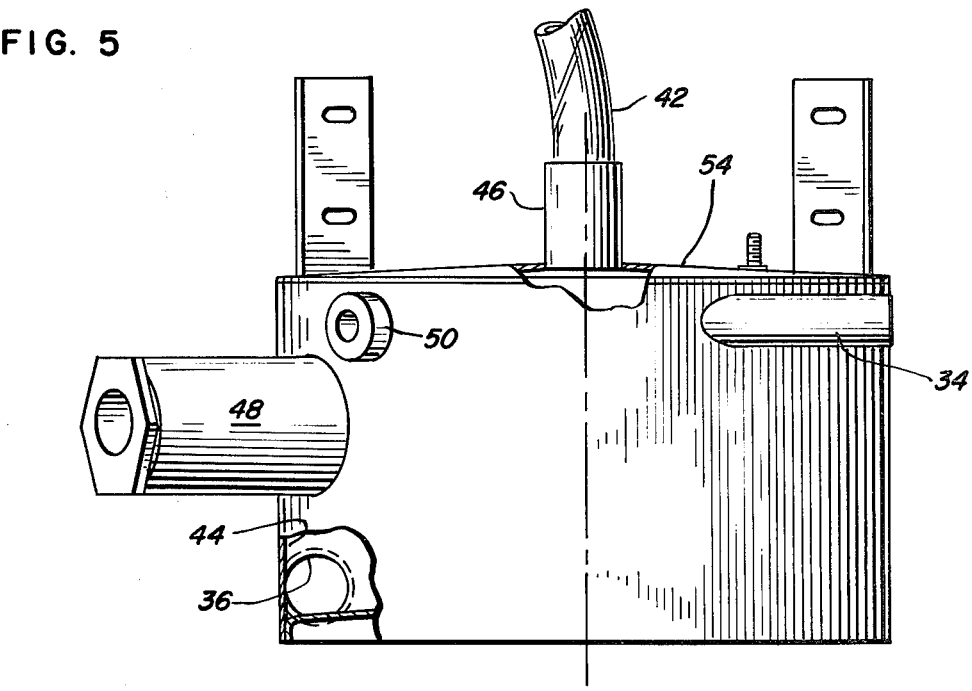
FIG. 5 is an elevational view, with portions broken away, of the bubble removing device of FIG. 4.

Referring now in particular to FIGS. 4 and 5, chamber 30, having a circular cross-section about longitudinal axis 42, is shown. Liquid inlet 34 is positioned to pass liquid into the chambers circumferentially about the side walls 44, to provide swirling of liquid in said chamber to force all gas bubbles and other low density materials to the center of the swirling liquid, from where they are removed or vented through port and conduit 46, which is positioned adjacent longitudinal axis 42.

Heater 48, which may be an electric cartridge resistance heater, penetrates into chamber 30, and is positioned so that the swirling liquid passes across it, for uniform and gentle heating of the moving liquid. Thermistor 50 is also mounted in chamber 30 to sense the temperature of the swirling liquid. Appropriate conventional circuitry is provided to cause heater 48 to operate in a manner responsive to temperature sensing by thermistor 50, to cause the swirling dialysis liquid to be brought to a desired, pre-determined temperature. Tip 52 of inlet 34 is spaced by about one quarter inch from side wall 44 of chamber 30, to reduce the drag which could be imparted by side wall 44 on the circumferentially swirling liquid passing from inlet 34.

Outlet 36 which leads to pump 32 is also circumferentially positioned in a manner to receive the swirling liquid directly into outlet 36, for example at a flow rate of 12–15 liters per minute. As shown in FIGS. 4 and 5, outlet 36 is positioned in a circumferential direction opposite to the circumferential direction of liquid inlet 34, for efficient receiving of the swirling liquid, and may be positioned below liquid inlet 34 in position of use as shown in FIG. 5. Furthermore, heater 48 is positioned above outlet 36, so that the small bubbles generated by the heating of the swirling liquid are not captured by outlet 36, since they tend to rise and to gravitate toward longitudinal axis 42. This provides further assurance that the liquid received by outlet 36 is bubble-free.

Top 54 of chamber 30 is slightly domed to provide further opportunity for bubbles to migrate inwardly to venting port 46, from where they rise through venting port 46 to the surface of the liquid. This surface is located at point 56, corresponding to the liquid level in storage tank 21.

The vented bubbles pass upwardly within conduit 46, past restricter 58, into conduit 60. From there, the gas may be freely vented through venting conduit 62, which is open to the exterior, and normally free of liquid.

Referring again to dialysis solution supply conduit 40, as described previously, bubble-free dialysis solution is impelled through this conduit by the action of pump 32. Liquid inlet 34 comprises restriction means in the second conduit passing from pump 32 back to chamber 30, since it constitutes a tube having a smaller inner diameter (e.g. 0.37 inch) than the inner diameter of outlet port 36, which in this embodiment may be 0.63 inch. As a result, pump 32 encounters a substantially greater flow resistance at its outlet than at its inlet, resulting in an increased pressure which may be used to propel dialysis solution through conduit 40. This relative restriction also accelerates liquid returned to chamber 30, for better swirling action.

Also, it is desirable for pump 32 to be no vertically higher than liquid inlet 34, so that air bubbles in the pump may be easily passed through outlet 34 and vented through port and conduit 46.

Accordingly, the bubble removing device of this invention operates to provide fresh, bubble-free dialysis solution under pressure to conduit 40, while the bubbles themselves are vented at atmospheric pressure through conduit 46.

Turning to the operation of the dialysis delivery system of this invention, for the first few minutes of operation, preferably about 5 minutes, the dialysis system may be actuated by recycle solenoid valve 64 to recirculate dialysis solution from line 40 back to storage tank 21, to insure that the dialysis solution concentrate which has been added to water in the tank 21 is adequately mixed. Following this, solenoid valve 64 is closed, to permit dialysis solution to flow upwardly past solenoid 64 in large quantity into conduit 66. Thermistor type temperature monitoring unit 68 monitors the dialysis solution temperature. The solution then passes through filter 70 to junction 72, one branch of which is controlled by a by-pass solenoid valve 74.

To dialyze in the single-pass mode, providing solution to dialysis unit 16, solenoid 74 is closed so that the dialysis solution passes through restricting flow valve 76, such as a needle valve. This permits positive displacement pump 78 (shown herein to be a gear pump) to impose a sub-atmospheric pressure on dialysis unit inlet line 80, dialysis unit 16, and outlet line 82. When desired, another bubble removing unit may be placed along inlet line 80 to remove any bubbles generated by the change in pressure of the dialyzate from above atmospheric to sub-atmospheric.

Pressure-sensing transducer 84 provides by conventional means a reading of the pressure on panel 13. A by-pass and one-way valve 86 is provided to recycle fluid from the outlet to the inlet of pump 78 in the event of a blockage somewhere in the line downstream of pump 78.

Outlet line 88 from by-pass pump 78 leads to a flowmeter 90, which is shown to be of the floating ball type, and which is adjacent a flow control valve 92. Line 94 then leads from valve 92 to container 18, which may contain a coil-type dialysis unit 14, particularly when the alternate mode of operation of the unit of this invention to be described below is utilized. In the mode of operation presently under discussion, container 18 serves as a bubble removing reservoir for the spent dialysis solution.

The solution then passes from container 18 into line 96, through blood leak transducer 98, which must be bubble-free in order to avoid false positive readings.

The spent dialysis solution is then shunted to line 100 because valve 102 is closed in this mode of operation. From there, the bulk of the dialysis solution passes upwardly through open valve 103, thereafter passing through conduit 104 to drain line 62.

In the present embodiment, a small amount of spent dialysis solution may pass through the right hand extremity of line 100 to and through pump 108, but, upon the termination of dialysis, that spent dialysis solution will be drained.

Accordingly, in the mode of operation described above, dialysis solution is provided on a single pass basis to dialysis unit 16.

When it is desired to provide dialysis solution through dialysis unit 14 in the recirculating-single pass mode, solenoid valve 74 is opened and, if desired valve 76 is completely closed. The dialysis solution passes through conduit 88 to flow meter 90, and from there through conduit 94 to container 18. Little or no dialysis solution passes through by-pass line 86 when the flow is under low pressure which is insufficient to pass through the spring loaded check valve of line 86.

Accordingly, fresh dialysis solution may be continuously supplied to container 18. Simultaneously, pump 108 provides recirculating flow of dialysis solution into dialyzer 14 through conduit 110, passing by a thermistor temperature measuring means 112, which temperature may be recorded on panel 13.

The dialysis solution spills out of the top of dialyzer 14 as indicated at 114, to join dialysis solution 116 already present in container 18. Dialysis solution is withdrawn through line 96, past blood leak detector transducer 98, and into line 100, back to the inlet of pump 108, with valve 102 being in closed position. Valve 103 is in closed position so that excess dialysis solution flows through conduits 104 and 62 respectively to the drain in an amount that approximates the inflow of dialysis solution through line 94, for recirculating single pass dialysis.

Overflow standpipe 118 is provided to prevent overfilling of container 18. As shown, liquid flowing into standpipe 118 passes through check valve 106 and from there out through conduits 104 and 62 to drain from the device. Access port 124 is provided for access to clean blood leak detector transducer 98.

When it is desired to flush the entire device for cleaning, pumps 32, 78 and 108 are operated with all valves open, to circulate dialysis solution and drain it through conduit 62. Container 18 can be drained by opening valve 102.

When it is desired to drain the entire device, pump 120 is activated to pass liquid upwardly along conduit 60, permitting liquid to drain through branch drain line 122, which communicates with draining conduit 62. The remaining fluid pumped by pump 120 is prevented from passing in large amounts into conduit 46 by the presence of restricter port 58. However, that amount of fluid which does so pass into conduit 46 can be recycled through outlet 36 back into conduit 22 for draining by pump 120. Fluid is prevented from passing back to container 18 by means of a one-way valve 106 which is shown here as a ball-type check valve. Accordingly, since the liquid in tank 21 is in flow communication with pump 120, the bulk of such liquid can also be drained through conduit 62.

The last remaining amount of liquid in the device can be drained by opening drain valve 24 for final drainage.

Accordingly, the dialysis solution delivery system of this invention provides a flexible system for permitting various types of dialysis, in particular the single pass technique and the recirculating-single pass technique of dialysis. Bubble-free dialysis solution is provided by a novel apparatus, in which the dialysis solution can be vented into the atmosphere while still being provided under pressurized condition for use in a dialysis unit.

The above has been offered for illustrative purposes only, and is not intended for the purpose of restricting the invention of this application, which is as defined in the claims below.

We claim:

1. In a dialysis delivery system which comprises a dialysis solution source, means for conveying dialysis solution from said source to a dialysis unit at a predetermined pressure and rate of flow, the improvement comprising: bubble separation apparatus positioned in flow communication with said dialysis solution source and said dialysis unit for removing any gas bubbles in said dialysis solution before they reach said dialysis unit, said bubble separation apparatus comprising a liquid storage chamber having side walls of generally circular cross-section about a longitudinal axis, and a port for removing said bubbles positioned adjacent the longitudinal axis of said chamber, said device also having a liquid inlet to said chamber which is positioned to pass liquid into said chamber circumferentially about said side walls, to provide swirling of liquid passing into said chamber, outlet and positive pressure pump means for removing bubble-free liquid from said chamber at a point spaced from said inlet but adjacent said side wall; liquid heating means positioned in said chamber to heat said swirling liquid to increase gas bubble generation; first conduit means for conveying a portion of bubble-free liquid so removed to a desired site of use and thereafter to a drain line, and second conduit means for conveying the balance of said bubble-free liquid so removed to the liquid inlet for reentry into the chamber, to enhance swirling action of fluid in said chamber.

2. The apparatus of claim 1 in which said conduit means for returning the balance of said bubble-free liquid to the inlet includes flow restriction means, to permit the creation of a positive pressure upstream of said restriction means by said pump means, for providing pressurized liquid to said first conduit means.

3. The apparatus of claim 2 in which said venting means adjacent the longitudinal axis of said chamber is also adjacent the axis of liquid swirling within said chamber and comprises an elongated, up-standing conduit for receiving pressurized liquid from said container, to provide a pressure head so that liquid does not spill from said container through the upstanding conduit.

4. The apparatus of claim 3 which has an additional liquid replenishment conduit communicating with said chamber, for connection to a liquid source for replacement into said chamber of liquid delivered through said first conduit.

5. The apparatus of claim 4 in which said additional liquid replensihment conduit communicates with said outlet means upstream of the positive pressure pump means.

6. The apparatus of claim 4 in which said inlet conduit is positioned adjacent the upper end of said chamber in position of use; said outlet means is positioned at a lower end of said chamber; and said heating means is spaced from said lower end, whereby bubbles generated from liquid by said heating means do not pass through said outlet means in normal operation.

7. The apparatus of claim 6 in which said liquid inlet is spaced from said side walls to facilitate swirling action of liquid passing into said storage chamber through said liquid inlet.

8. The apparatus of claim 9 in which said liquid inlet is vertically positioned relative to said pump means so that air is not trapped in said pump means.

9. The dialysis delivery system of claim 1 including a liquid storage tank, and a replacement liquid conduit communicating between said storage tank and the outlet means, upstream of said positive pressure pump means.

10. A method for providing a continuous supply of degassed dialysis solution to a dialyzer comprising:
 (1) providing a reservoir of dialysis solution from which a predetermined amount of solution may be drawn;
 (2) conveying a first portion of said dialysis solution tangentially through an inlet into a chamber of generally circular cross section while simultaneously heating said first portion in an area adjacent said chamber to facilitate the forming of bubbles;
 (3) swirling said solution within said chamber to cause said gas bubbles formed in said solution to migrate toward the center of swirling liquid;
 (4) venting said gas bubbles from the center of said swirling solution in said chamber to produce a substantially degassed first portion;
 (5) after said heating, swirling, and venting, conveying said degassed first portion out of said chamber and conveying a part of said degassed first portion to a dialyzer;
 (6) supplementing the balance of said degassed first portion with supplemental solution from said reservoir at a flow rate substantially equal to that of said degassed first portion conveyed to the dialyzer; and
 (7) recirculating the balance of said degassed first portion with said supplemental solution to the inlet of said chamber.

* * * * *